United States Patent
Dey et al.

(10) Patent No.: US 6,915,623 B2
(45) Date of Patent: Jul. 12, 2005

(54) METHOD FOR ASSEMBLING A PACKAGE FOR SUTURES

(75) Inventors: Clifford A. Dey, Riegelsville, PA (US); Robert J. Cerwin, Pipersville, PA (US); Thomas Warner, Milroy, PA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/641,536

(22) Filed: Aug. 14, 2003

(65) Prior Publication Data

US 2005/0034431 A1 Feb. 17, 2005

(51) Int. Cl.⁷ .............................................. B65B 51/22
(52) U.S. Cl. .......................... 53/478; 53/430; 53/329.3
(58) Field of Search ........................ 53/430, 478, 329.3

(56) References Cited

U.S. PATENT DOCUMENTS

| | | | |
|---|---|---|---|
| 3,728,839 A | | 4/1973 | Glick |
| 3,815,315 A | | 6/1974 | Glick |
| 3,959,947 A | | 6/1976 | Sonnino |
| 5,040,357 A | * | 8/1991 | Ingemann et al. ............. 53/478 |
| 5,090,180 A | * | 2/1992 | Sorensen .................... 53/329.3 |
| 5,111,641 A | | 5/1992 | Brown et al. |
| 5,345,747 A | * | 9/1994 | Raque et al. ................. 53/478 |
| 5,675,961 A | * | 10/1997 | Cerwin et al. ................ 53/430 |
| 5,868,244 A | | 2/1999 | Ivanov et al. |
| 6,047,815 A | * | 4/2000 | Cerwin et al. ............. 206/63.3 |
| 6,081,981 A | * | 7/2000 | Demarest et al. ........ 29/407.08 |
| 6,135,272 A | * | 10/2000 | Sobel et al. ............... 206/63.3 |
| 6,205,748 B1 | * | 3/2001 | Daniele et al. ............... 53/430 |
| 6,463,719 B2 | * | 10/2002 | Dey et al. .................... 53/430 |

* cited by examiner

Primary Examiner—John Sipos

(57) ABSTRACT

A novel method and apparatus for riveting a two-piece suture tray package. A two-piece suture tray assembly is provided having a top member and a bottom member. The top member has a top and a bottom, and plurality of rivet members extending down from the bottom of the top member. The rivet members have free ends. The bottom member has a top and a flat bottom surface, and a plurality of rivet receiving openings extending therethrough. A counterbore surrounds each rivet receiving opening in the flat bottom surface. An ultrasonic riveting apparatus is provided having a clamp member with a cavity, and an ultrasonic horn member having a flat bottom moveably mounted in the cavity. The assembly is mounted in the riveting apparatus and engaged by the clamp member. The flat bottom of the horn member engages the free ends of the rivet members, and when energized by an ultrasonic generator, causes the free ends of the rivet members to deform into the counterbores, such that the free ends are flat and in alignment with the bottom surface of the bottom member.

7 Claims, 10 Drawing Sheets

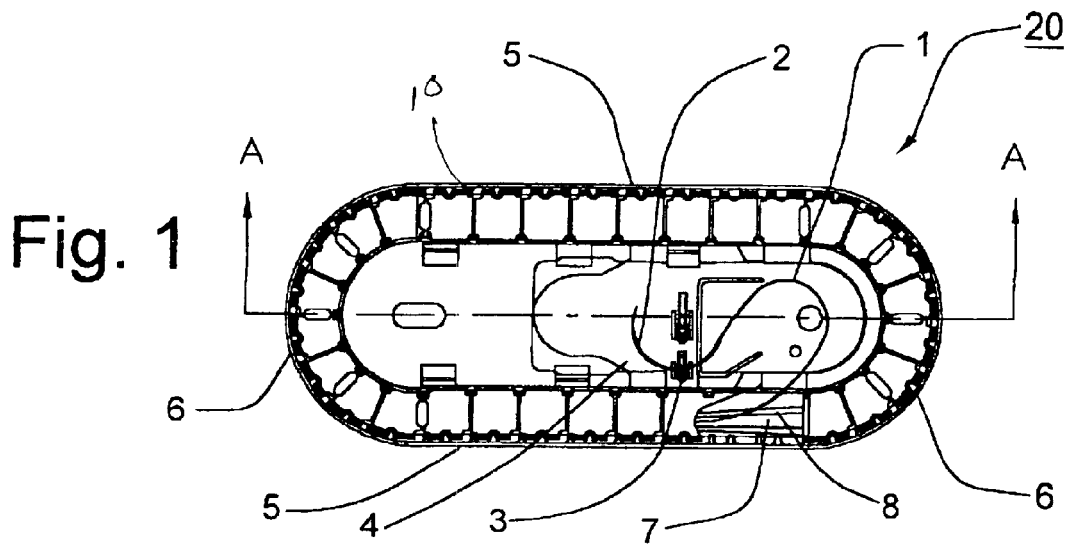
Fig. 1
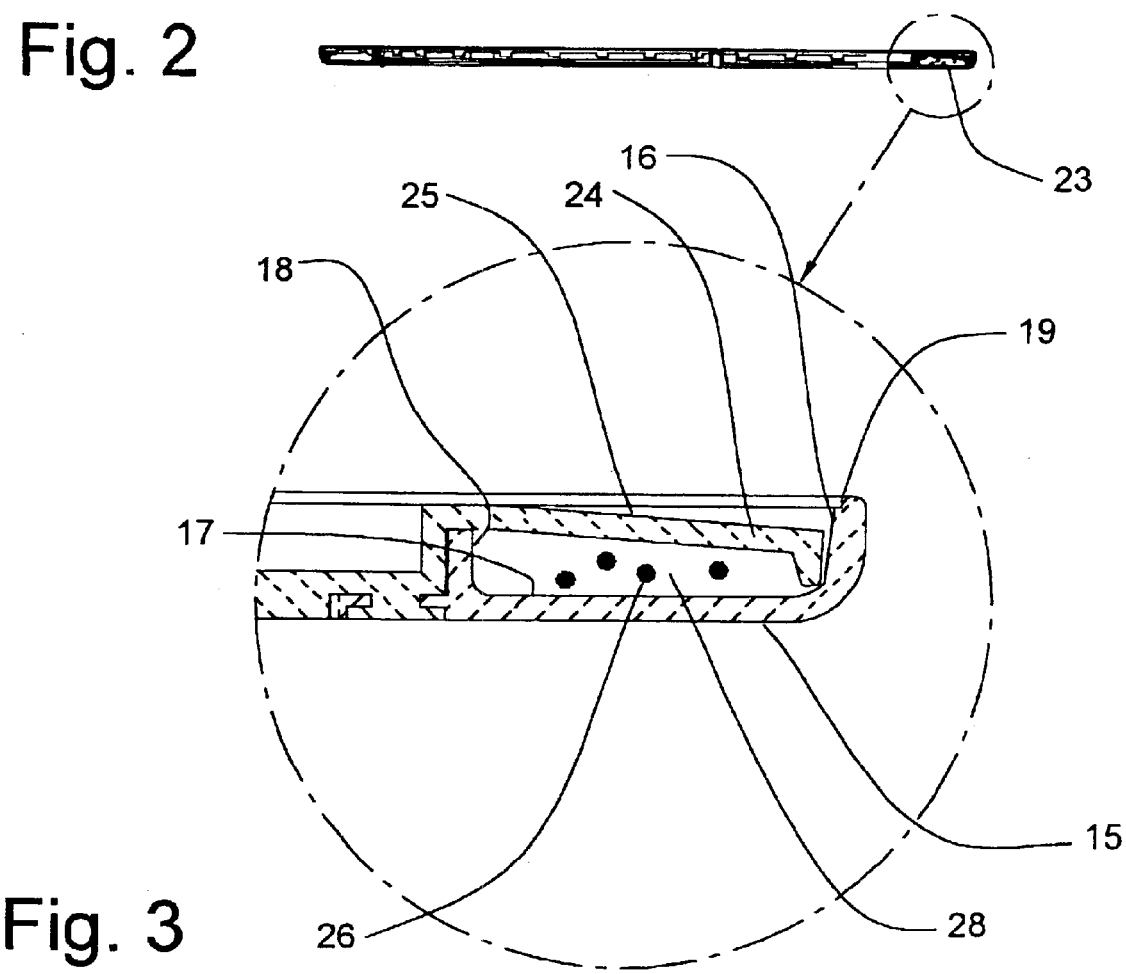
Fig. 2
Fig. 3

METHOD FOR ASSEMBLING A PACKAGE FOR SUTURES

TECHNICAL FIELD

The field of art to which this patent application relates is methods for assembling packages, in particular, method of assembling packages for sutures.

BACKGROUND OF THE INVENTION

Packages for surgical sutures are well known in the art. The function of the package is to contain and protect the suture strand material, and any attached surgical needles, and to provide low-force, tangle-free dispensing when used by the health care professional in a surgical procedure. One type of package that is known in this art is a tray package having a suture channel. Suture is loaded into the package by winding the suture into a suture channel, typically having an oval configuration. Suture tray packages are disclosed in U.S. Pat. Nos. 6,047,815 and 6,135,272, which are incorporated by reference. It is preferable that the package dispense the suture strand in a form that is relatively straight, retaining a minimal amount of 'memory', of the coiled shape of the suture packaged in the suture channel.

A further function of a suture package is to secure an attached surgical needle in a holding device, or 'needle park', which secures the needle in a readily accessible location with sufficient strength to withstand shipping and handling forces to which the package may be exposed prior to use, while presenting access to and easy removal of the needle by the surgeon. It is desirable that the package be relatively thin, so that an efficient quantity may be stacked together within the confines of a dispenser carton. A dispenser carton is typically limited in size by a conventional hospital operating room storage rack system.

The package also must provide a substrate for appropriate and required labeling. It is also important that the package be readily manufacturable. Surgical sutures are cost sensitive, high volume, disposable products. Accordingly, the packaging should present maximum function for minimal cost.

Packages designs that incorporate the previous-described features typically have intricate shapes that are best provided by a tray-like base component made from a precision plastic injection molding. Still more design features can be provided if the molded package has two components, a top member and bottom member. Advantages of a two-component design are that more shapes and features can be incorporated into the resulting assembly, thereby providing a better opportunity to achieve the package objectives. A further advantage of a two-piece design is that different materials may be used for the two components, for example, a flexible plastic for the top member embodying hinged doors, and a more slippery rigid plastic (e.g., styrene polymer), for the bottom member embodying a suture track that is sensitive to sliding friction.

The assembly operation for a two-component package requires an efficient and secure method of joining the components. Typical attachment methods for molded plastic parts which are adaptable to full automation include, but not limited to, conventional ultrasonic welding, solvent or adhesive welding, various snap-together designs, and use of mechanical fasteners such as screws.

Although the conventional methods and processes for attaching components of tray packages together are adequate for their intended purpose, there is a continuing need in this art for improved attachment methods and processing.

SUMMARY OF THE INVENTION

Therefore, it is an object of then present invention to provide a process for joining together a two-piece tray package for surgical sutures.

Another object of the present invention is to provide an attachment method for suture package moldings that is fast to apply, thereby not slowing down, for example, a connected molding machine or other piece of process equipment.

Yet another object of the present invention is to provide a novel low manufacturing cost process, not requiring added parts or materials such as fasteners.

Still yet another object of the present invention is to provide a novel process that minimizes the thickness of a suture tray package and that it provides a secure bond at critical locations on the package.

Another objective of the invention is to provide a novel package assembly process that is compatible with high speed automated assembly machinery.

Accordingly, a novel method of joining together a two-part suture package is disclosed. The novel method is preferably directed toward a method of riveting a two-component suture tray package, but may be used to assembly or join together other types of two-component packages. In the novel method of the present invention, a top component is provided. The top component has a top, a bottom, an outer periphery and a plurality of rivet members extending down from the bottom. The rivets having bottom ends. A bottom component is provided. The bottom component has a top, a substantially flat bottom, an outer periphery, a suture channel, and a plurality of rivet receiving holes extending through the bottom component for receiving the rivet members. There is a counter bore extending into the bottom of the bottom component around each rivet receiving hole.

The top component and the bottom component are assembled together to form an assembly by substantially aligning the peripheries of the top and bottom components and aligning the rivet members of the top component with corresponding rivet receiving holes of the bottom member, and then moving the top and bottom components together such that the rivet members are substantially contained in the rivet receiving holes and counterbores surrounding the rivet receiving holes. An ultrasonic riveting apparatus is provided. The apparatus has a a frame. A clamp member is movably mounted to the frame. The clamp member has a cavity, a bottom surface, a top surface and openings in the top and bottom surfaces in communication with the cavity. A base is mounted to the frame for receiving the assembled bottom component and top component. The base has a top, a bottom, and a groove in the top for receiving the suture channel of the bottom component. An ultrasonic horn member is movingly mounted to the frame. The ultrasonic horn member has a substantially flat bottom surface. The ultrasonic horn member is moveable within the cavity of the clamp member. An ultrasonic generator connected to the horn member. The assembly is placed on the base member such that the bottom component is on top of the top component and the suture channel is substantially contained within the groove. The clamp member is moved to engage the bottom of the bottom member of the assembly. The ultrasonic horn member is moved through the cavity of the clamp member such that the bottom surface of the horn member engages the free end of each rivet member. And, the horn member is energized with sufficient ultrasonic energy for a sufficient period of time to effectively heat and deform the free ends of the rivets such that the free ends of the rivets are contained within the counterbores surrounding the rivet holes, and the ends of the rivets are substantially flat and in alignment with the flat bottom surface of the bottom component.

Yet another aspect of the present invention is a novel ultrasonic riveting apparatus. The ultrasonic riveting apparatus has a frame. A clamp member is movably mounted to the frame. The clamp member has a cavity, a bottom surface, a top surface and openings in the top and bottom surfaces in communication with the cavity. A base is mounted to the frame, the base has a top, a bottom and a groove in the top. An ultrasonic horn member is movingly mounted to the frame. The ultrasonic horn member has a substantially flat bottom surface. The ultrasonic horn member is moveable within the cavity of the clamp member. The apparatus also has an ultrasonic generator connected to the horn member.

These and other aspects and advantages of the present invention will become more apparent from the following description and accompanying drawings.

BRIEF DESCRIPTION OF THE DRAWINGS

FIG. 1 is an illustration of the suture package of the preferred embodiment, in plan view.

FIG. 2 is an illustration of the suture package of the preferred embodiment, in elevation view through Section A—A of FIG. 1.

FIG. 3 is an enlarged view of the suture track of FIG. 2.

DETAILED DESCRIPTION OF THE INVENTION

Figure 4:
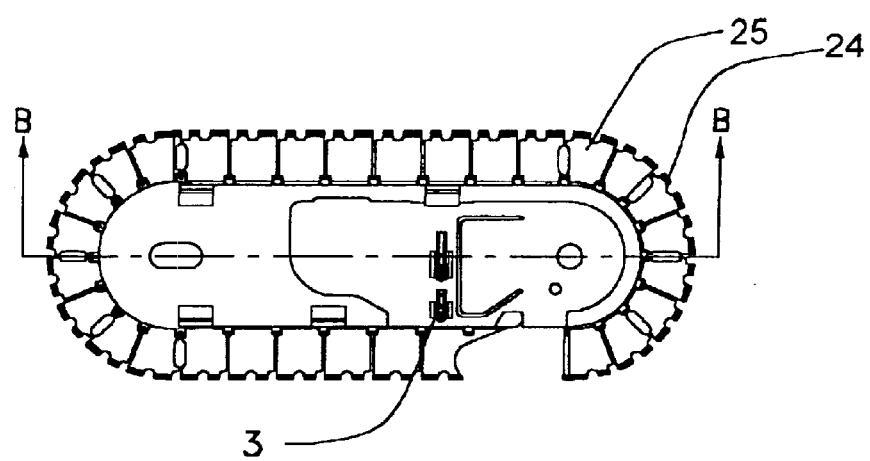
FIG. 4 is a plan view illustration of the top member.

FIG. 1 illustrates a plan view of a molded plastic suture package 20, further illustrating a suture 1 and attached needle 2 mounted therein. The needle 2 is secured in a needle park 3 molded into the floor 4 of the package 20. The outer periphery 10 of package 20 is seen to have substantially straight parallel sides 5 connected by opposed semicircular ends 6. Inboard of the outer periphery and parallel thereto is an internal, enclosed suture channel 7 containing the coiled suture loops 8.

Referring to FIG. 2, which is an elevation view of section A—A taken through FIG. 1, and FIG. 3, an enlarged view of the suture channel end portion 23 of FIG. 2 is illustrated.

The package 20 is seen to have an injection molded top and bottom members 24 and 15, respectively. Said bottom member 15 has a suture channel vertical outer wall 16, floor 17, vertical inner wall 18, and a peripheral recessed groove 19 for a label panel (not shown).

The top member 24 is seen to have a plurality of flexible doors 25 that form the suture channel top cover. The top member 24 also embodies the needle park (not shown) molded to the central base area. It is seen that the outer wall 16, floor 17, inner wall 18, and the top cover doors 25 define a hollow channel cavity 28 containing the suture strands 26 contained therein.

The bottom member 15 and top member 24 are molded in the same machine in multiple cavities simultaneously, and are joined together in an automated operation described hereinbelow.

FIG. 4 illustrates a plan view of the molded top member 24, prior to assembly to the package. Flexible doors 25 are disposed around the periphery thereof.

Figure 5:
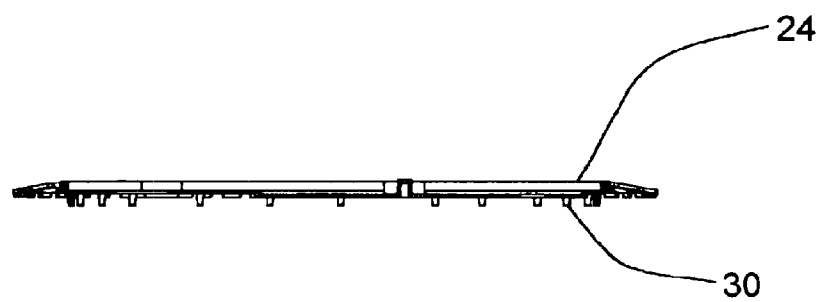
FIG. 5 is a sectioned elevation view of the top member of FIG. 4 taken through section B—B.

FIG. 5 is an elevational, side view of section B—B taken through the top member 24 of FIG. 4. A plurality of molded rivet pins 30 are seen projecting from the underside thereof.

Figure 6:
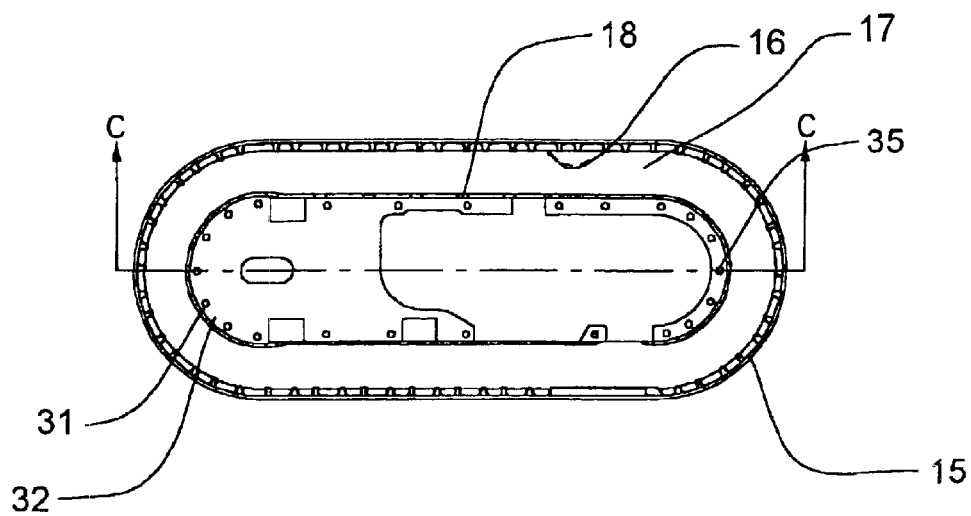
FIG. 6 is a plan view illustration of the bottom member.

FIG. 6 illustrates the bottom member 15 of the package, prior to package assembly. A plurality of rivet holes 31 projects through the base material 32 of the bottom member 15. The location of the rivet holes 31 correspond to the rivet pins 30 of the top member 24 of FIG. 5. It is seen that the preferred embodiment illustrated comprises twenty-three rivet holes 31 spatially positioned at locations on the package bottom member 15 where secure clamping force is most beneficial to the package 20 function.

Figure 7:
FIG. 7 is a sectioned elevation view of the bottom member of FIG. 6 taken through section C—C.
Figure 8:
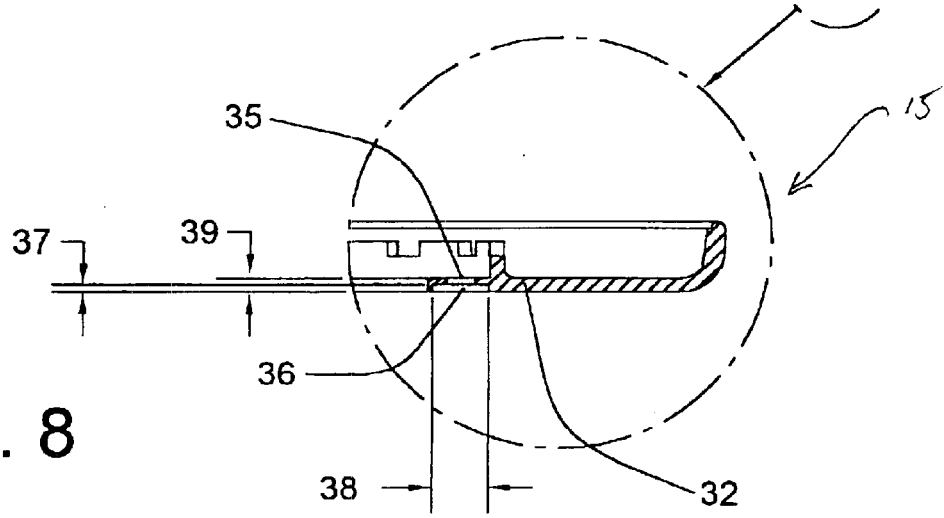
FIG. 8 is an enlarged view of a rivet hole in FIG. 7.

FIG. 7 is an elevation view of section C—C taken through FIG. 6, and FIG. 8 is an enlarged view of the section containing one example 35 of the rivet holes 31 seen in FIG. 6. It is seen that a counterbore 36, molded into the thickness 39 of the package base material 32 surrounds the rivet hole 35. The counterbore 36 is seen to have a depth 37 and diameter 38. Each rivet hole 31 has a similar counter bore 36.

Figure 9:
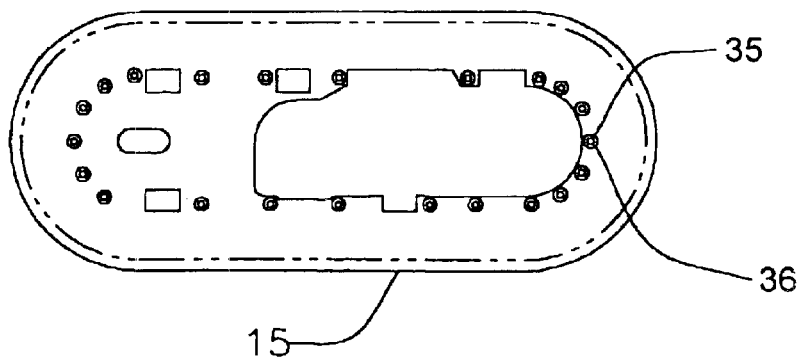
FIG. 9 is an underside view of the bottom member illustrating the counterbores in the rivet holes.

FIG. 9 is an underside view of the bottom member 15 of FIG. 6 illustrating the rivet holes 31, particularly pointing out rivet hole 35, and the counterbores 36 coaxial therewith.

Figure 10:
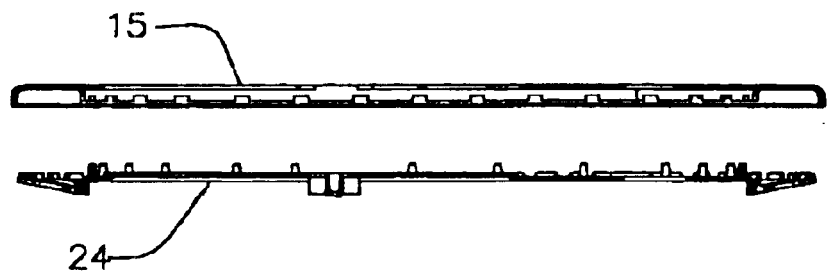
FIG. 10 is a sectioned elevation view of the top and bottom members aligned, prior to assembly.

FIG. 10 is an elevation view of the two sectioned package components 15 and 24 illustrated in FIGS. 5 and 7. In the assembly process of the preferred embodiment the assembly is inverted, with the bottom member 15 positioned on top, and top member 24 on the bottom as illustrated. The bottom member 15 is illustrated aligned with the top member 24 prior to assembly thereto.

Figure 11:
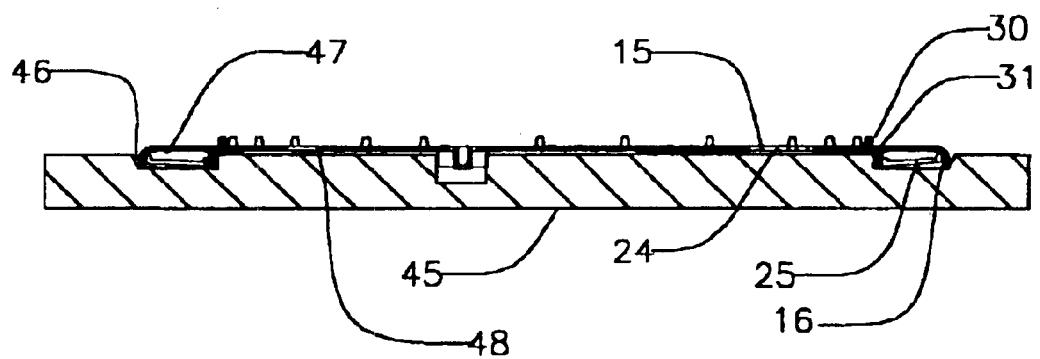
FIG. 11 is a sectioned elevation view of the top and bottom members nested and mounted on the riveting base.

Referring to FIG. 11, the bottom member 15 is seen nested into the top member 24, causing the plurality of rivet pins 30 to protrude through mating holes 31, and the suture channel doors 25 of said top member 24 to likewise nest within the outside vertical wall 16 of the bottom member 15. The assembly is seen mounted on the riveting base tool 45, said tool having an oval channel 46 therein to provide clearance for the molded suture channel structure 47. The riveting base tool 45 embodies a flat surface 48 to support the plurality of rivets 30, providing a backup force thereon during the riveting process. The base tool 45 is illustrated in a sectioned elevation view taken through the plane A—A of FIG. 1. Said plane A—A defining the sectioned view of FIG. 11 centrally cuts the end rivet 30 and rivet hole 31, enlarged below for detailed illustration.

Figure 12:
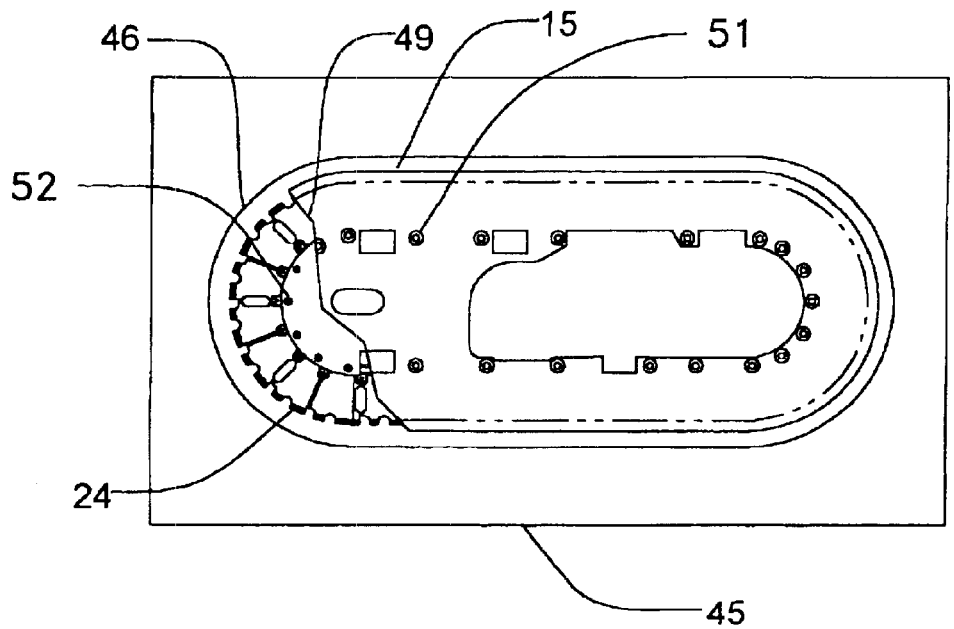
FIG. 12 is a plan view of the top and bottom members nested and mounted on the riveting base, with the bottom member partially cut away to illustrate rivet details.

FIG. 12 is a plan view of the bottom and top moldings, 15 and 24, and the base tool 45 of FIG. 11, illustrating the bottom member 15 cut away along break line 49 to view the top member 24 therebelow. An oval clearance groove 46 for the suture channel 47 (FIG. 11) is seen in the base 45. Rivet holes with rivet posts protruding up therethrough 51 are seen on the bottom member 15. Rivet pins 52 are seen protruding up from the top member 24.

Figure 13:
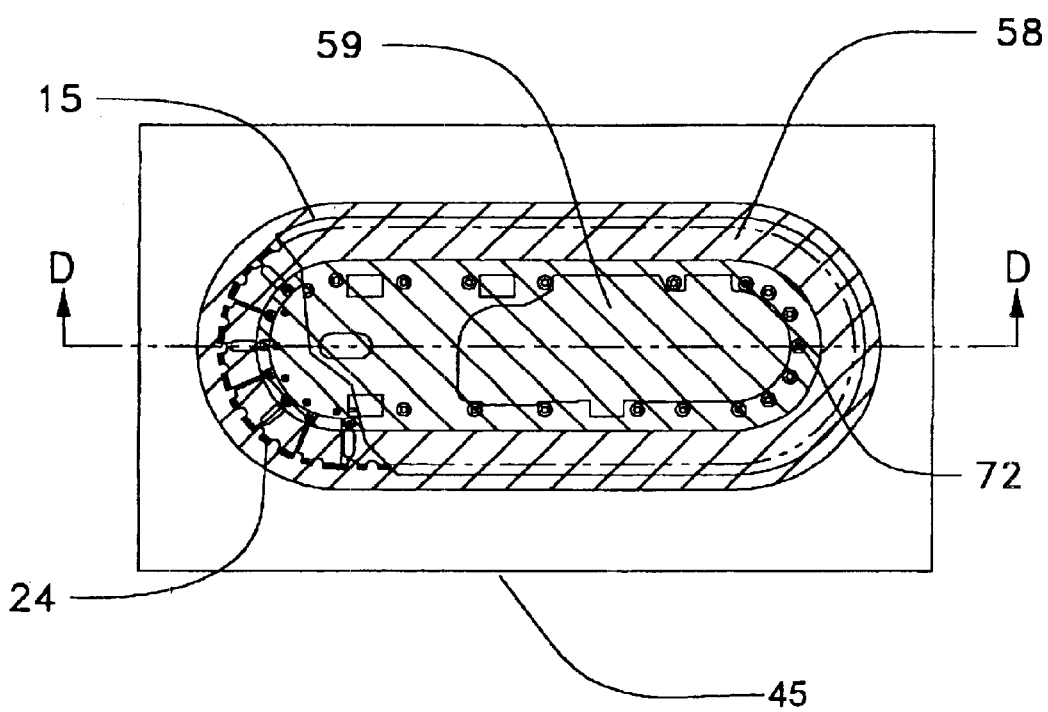
FIG. 13 is the illustration of FIG. 12 with the footprint of the clamp and ultrasonic horn indicated by shaded areas.

FIG. 13 is the plan view of the riveting base 45 of FIG. 12 with two shaded footprints illustrated thereover. Shaded area 58 is the area of the package suture channel 47 (FIG. 11) over which a clamping force is placed during the riveting operation. Shaded area 59 is the footprint of the flat ultrasonic welding horn positioned to heat form the rivet pins.

Figure 14:
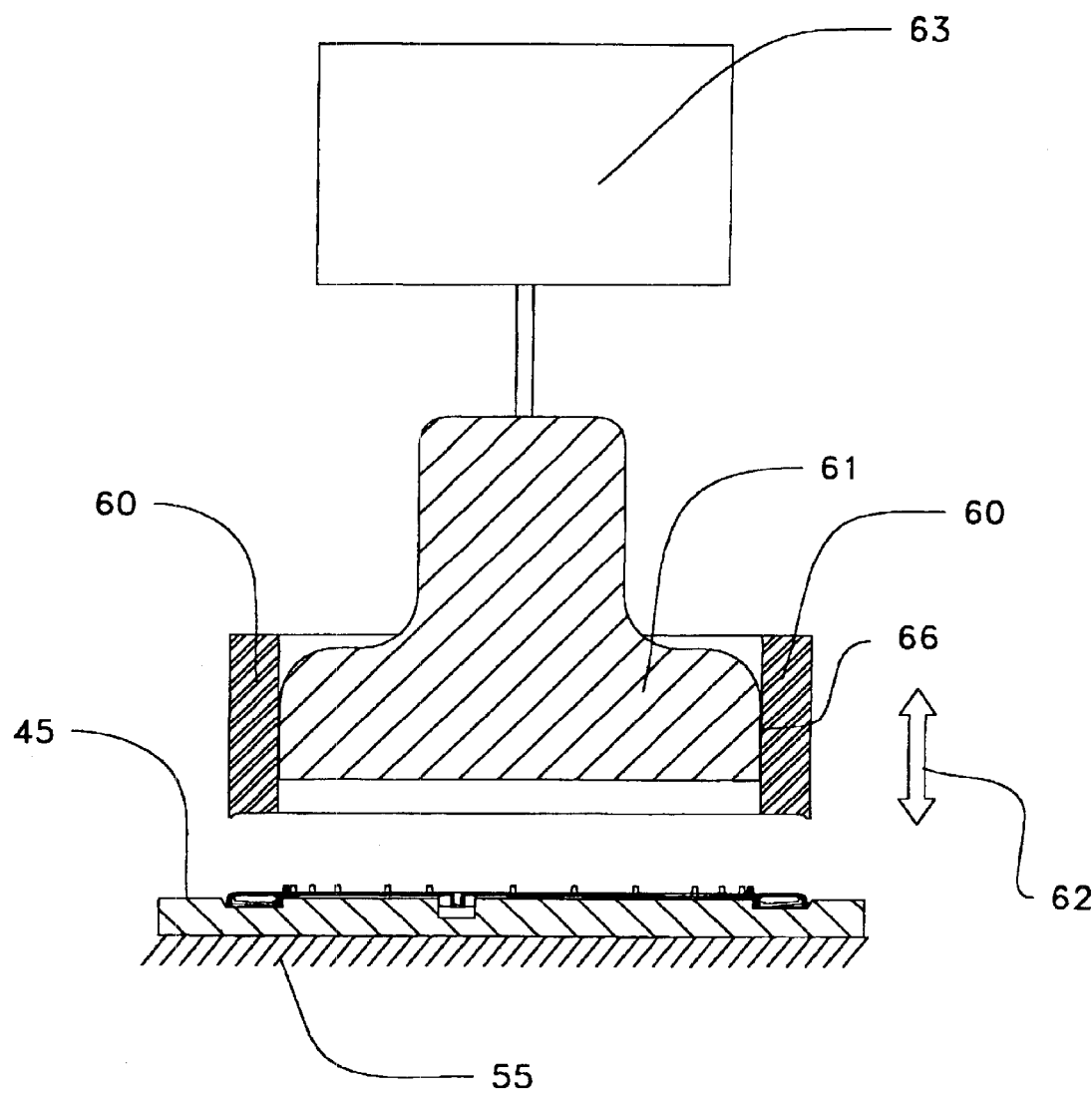
FIG. 14 is a sectioned elevation view of the riveting base and top and bottom members thereon of FIG. 11, with the clamp and the ultrasonic system illustrated.

Please refer to FIG. 14, which illustrates a section D—D taken through the base 45 of FIG. 13 with sectioned views of the clamping tool 60 and ultrasonic horn 61 added thereabove.

The ultrasonic horn 61 is seen to be energized by the conventional electronic ultrasonic generator 63. The clamp 60 is an oval hollow centered structure with a cavity 66 and the horizontal cross section of the shaded area 58 of FIG. 13. The Ultrasonic horn 61 is a flat-bottomed solid member with the rounded end shape of the shaded area 59, FIG. 13. Said clamp 60 and horn 61 are independently vertically moveable as indicated by the arrow 62, and have a clearance space 66 therebetween. The base tool 45 is horizontally slideable by an indexing transfer mechanism (not shown) and is supported by the frame of the machine 55 and thereby enabled to withstand downward forces.

Figure 15:
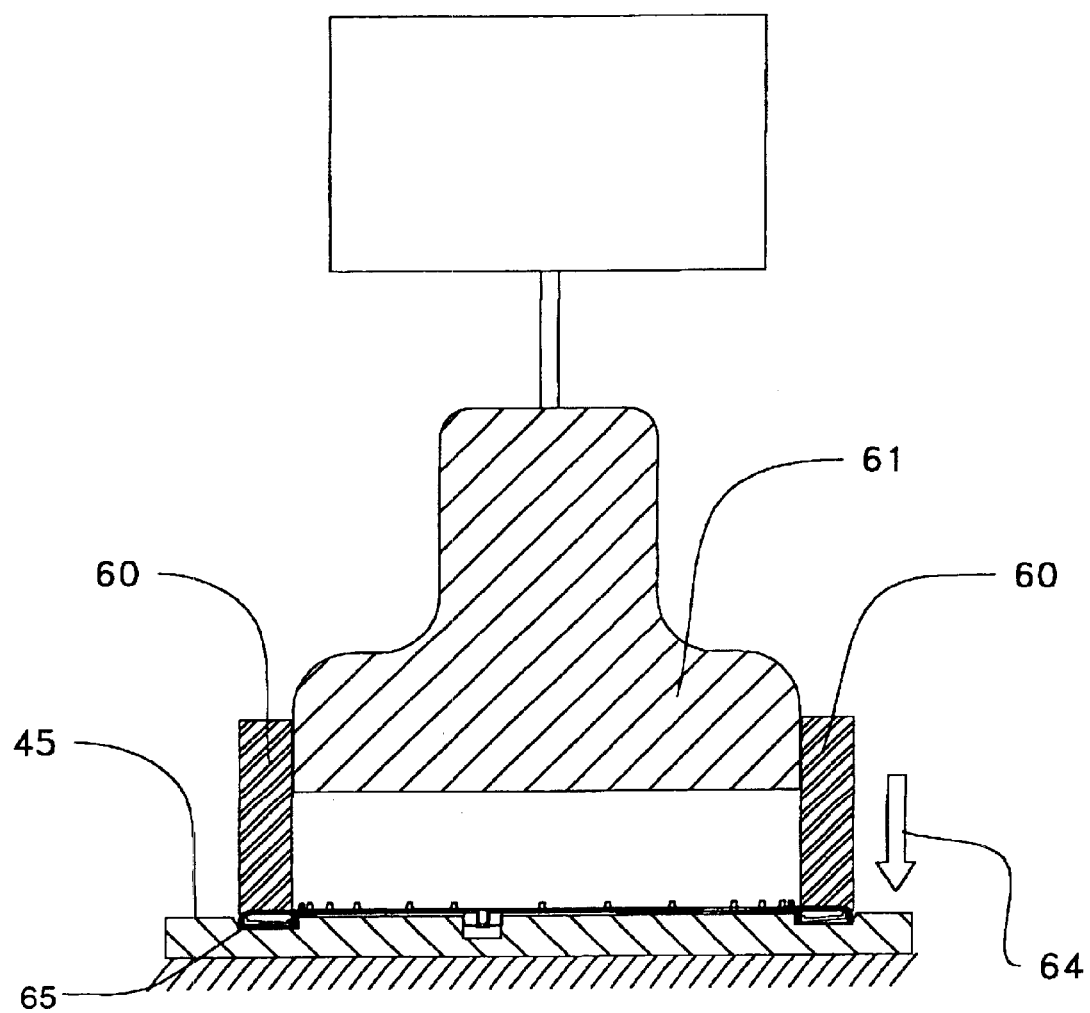
FIG. 15 is the sectioned elevation view of FIG. 14 with the clamp engaged.

FIG. 15 illustrates the initiation of the riveting cycle. The clamp 60 descends as indicated by arrow 64, exerting downward force on the suture track 65 around the periphery of the moldings, pressing same together and against the base tool 45 to assure there is no gap therebetween. The ultrasonic horn 61 remains in a vertical parked position.

Figure 16:
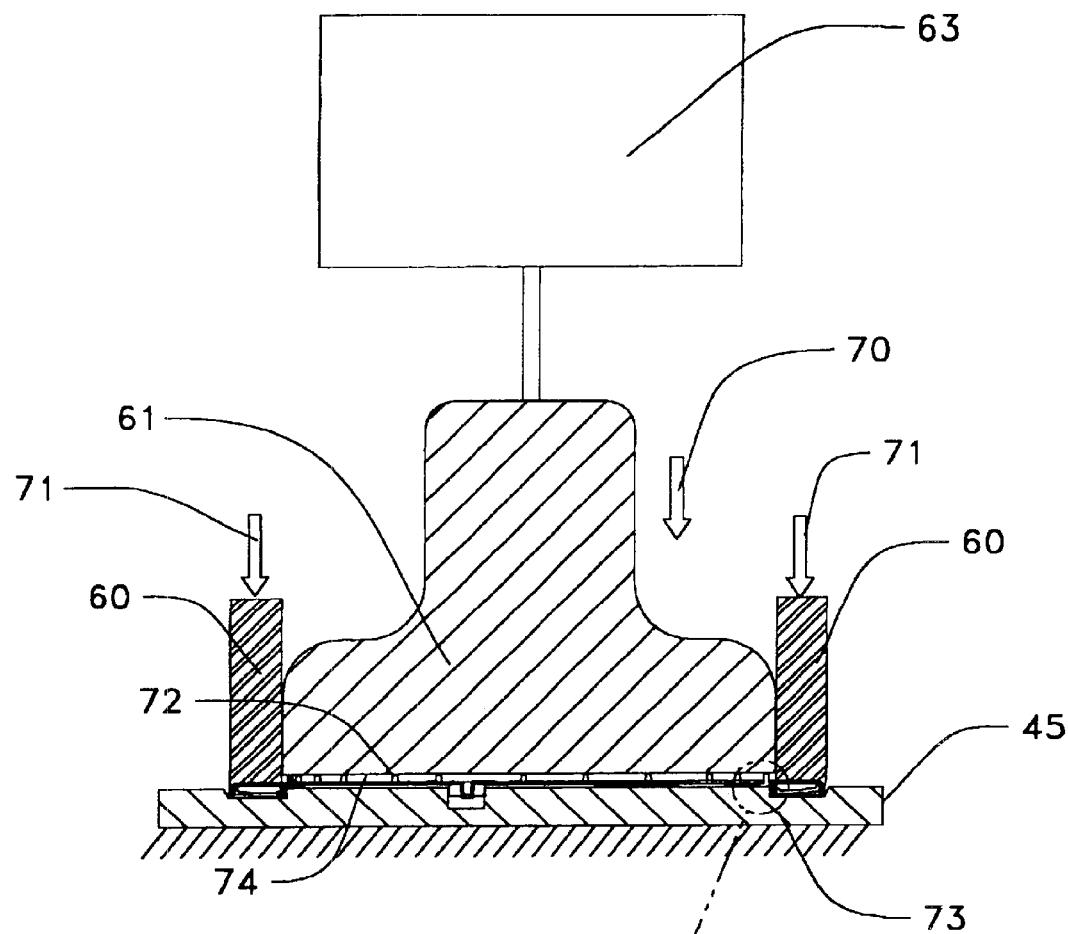
FIG. 16 is the sectioned elevation view of FIG. 15 with the ultrasonic horn lowered and bearing on the rivet posts.

FIG. 16 illustrates the next sequence in the riveting cycle. The ultrasonic horn 61 is displaced vertically downward indicated by the arrow 70 until the bottom surface 74 contacts the top of the rivet posts 72 and exerts a force thereon. Simultaneously the force by the clamp 60 illustrated by the arrows 71 is continued.

Figure 17:
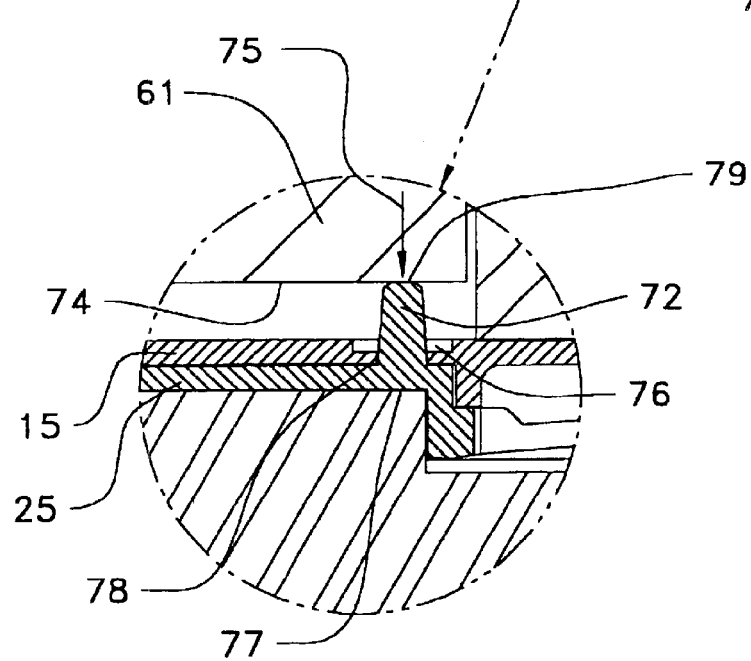
FIG. 17 is an enlarged view of one rivet and hole with counterbore of FIG. 16.

Please refer to FIG. 17, comprised of an area 73 in FIG. 16, enlarged to illustrate one single rivet, which can be seen in detail during the riveting process. The description relating to said single rivet pertains to the full plurality of rivets simultaneously.

FIG. 17 is an enlarged part of section D—D, FIG. 13, said section cutting through the rivet 72 and top and bottom package members 24 and 15 respectively. In FIG. 17 the rivet 72 is seen entered through the rivet hole 78 in the bottom member 15, said bottom member also having a counterbore 76 coaxial therewith. The upper surface 77 of the base 45 supports the rivet 72 as force is applied thereon.

The ultrasonic horn 61 descends, bringing the underside surface 74 thereof to contact the top 79 of the rivet 72.

The ultrasonic horn 61 can be driven downward by a pneumatic cylinder, servo driven slide, or other motion device. The downward force, indicated by arrow 75, sensed by suitable force transducers that send a signal to the control system (not shown), is increased to a predetermined trigger value that is sufficiently effective to produce a desired riveted connection.

Said trigger signal is programmed, through the control system, to initiate the heat cycle of the ultrasonic driver 63 for the horn 61 when the downward trigger force of the ultrasonic horn 61 is reached, thereby initiating heating of the rivet plastic material at the contact point 79.

Figure 18:
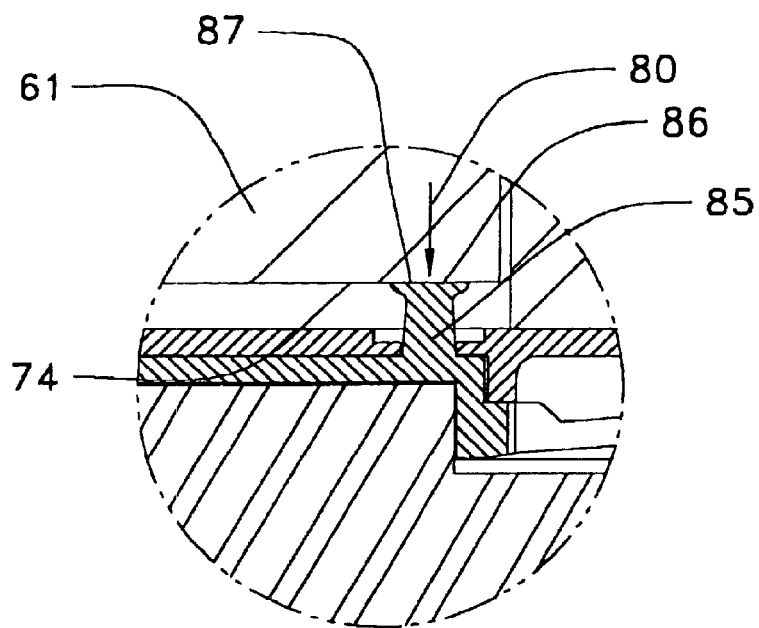
FIG. 18 is a view of the FIG. 17 enlargement illustrating the initial heat forming of the rivet.

FIG. 18 illustrates an enlarged view of FIG. 17 as heating of the rivet post 85 continues. Collapse and heat forming 86 of said rivet post is seen as heat from the horn 61 is imparted by the bottom surface 74 and force indicated by arrow 80 at the contact area 87 continues.

Figure 19:
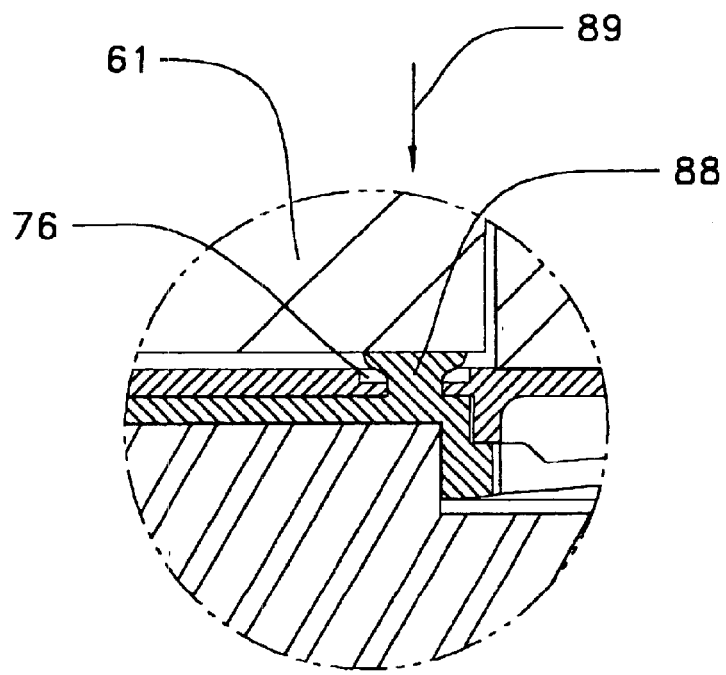
FIG. 19 is a view of FIG. 18 illustrating the rivet heat forming progressing, and the shape of the deformation thereof.

FIG. 19 illustrates the condition of FIG. 18, after further heat forming of the rivet 88 and downward movement of the ultrasonic horn 61 in the direction of arrow 89. The counterbore 76 is sized with a depth 37 and diameter 38 (FIG. 8) to contain the volume of reformed rivet material, seen in FIG. 20. Said counterbore 76 could be a countersink, or any volumetric geometric shape coaxial with the rivet hole 78 sized to contain the formed rivet material.

Figure 20:
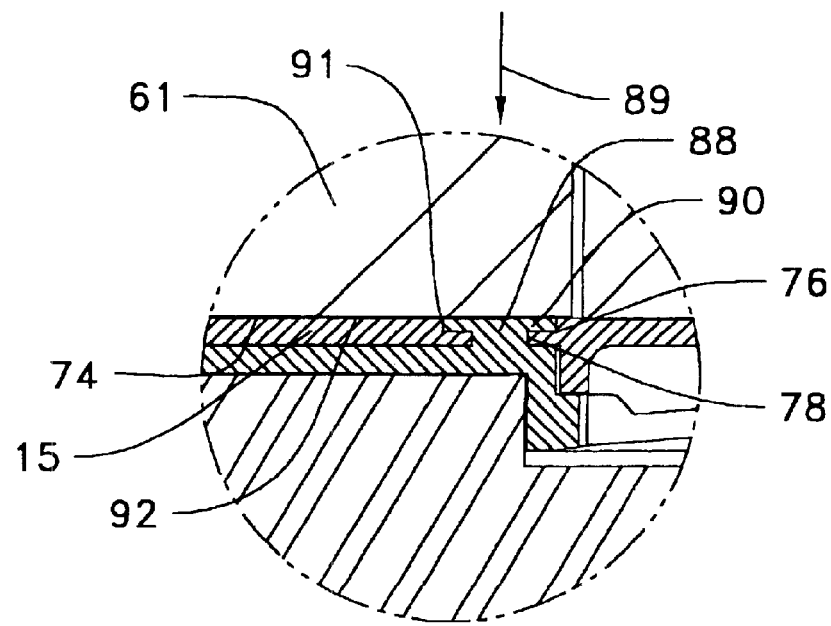
FIG. 20 is a view of FIG. 19 illustrating the end of the forming stroke, and completion of the riveting operation.
Figure 21:
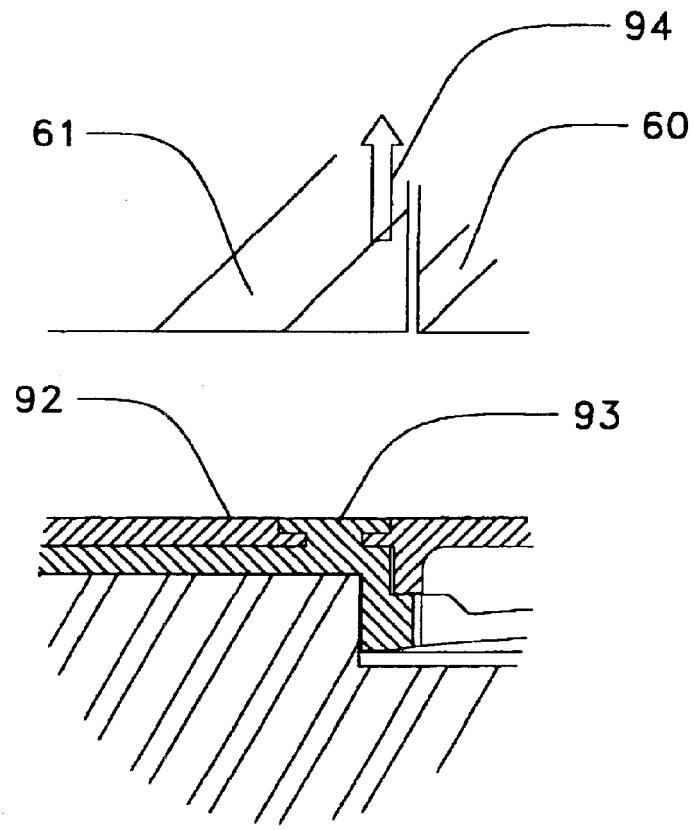
FIG. 21 illustrates the view of FIG. 20 after withdrawal of the rivet forming tooling and clamp, illustrating the flat surface with no gain in package thickness resulting from the riveting process.

FIG. 20 illustrates completion of the riveting process of FIG. 19. The rivet 88 is seen fully plastically formed 90 into and filling the counterbore 76 and rivet hole 78. Some melting and fusing (welding) of the rivet and the plastic material of the counterbore may take place at the interface 91 thereof. At the end of the ultrasonic horn 61 rivet forming stroke, in the direction of the arrow 89, the underside 74 of said horn contacts the surface 92 of the bottom member 15, thereby resulting in the surface 92 having no added thickness dimension from the rivets therein. Said flat surface 92 is seen in FIG. 21, illustrating the end of the riveting cycle, and the ultrasonic 61 and clamp 60 raised in the direction of arrow 94.

The riveting process illustrated in the above enlarged views of one rivet is simultaneously applied to all rivets on the package, and possibly multiple packages ganged together in multiple part tooling. Forms of heating other than ultrasonic may be used, such as heated plates or punches. It is further seen that the orientation of the products and tooling described hereinabove is arbitrary, and could have been inverted or lateral, as long as the relative motions described are achieved. The round rivet cross section of the preferred embodiment could be rectangular, ellipsoid, triangular, or any other geometric shape. Further, welding or fusing of the two plastic materials in the top and bottom members need not take place, and the two members could be of different materials. The bottom member need not be plastic, but could be made from a number of rigid materials such as metal.

An example of a conventional ultrasonic generator that can be used with the riveting apparatus of the present invention is a Bronson ultrasonic generator model No. 921AES manufactured by Branson Ultrasonics, Danbury, Conn., U.S. The amount of ultrasonic energy transmitted to the rivet members by the bottom of the horn member will be sufficient to effectively deform the rivet members into the counterbores on the bottom of the bottom component. The energy will vary depending upon the size and number of the rivet members and the material of construction of the rivet members.

The top and bottom members of the tray package assemblies that are riveted using the process of the present invention are typically manufactured from conventional polymeric materials including high density polyethylene, polypropylene, polystyrene, polycarbonate and the like and the like. The top and bottom members may be manufactured from the same materials or different materials. The top and bottom members are preferably made by conventional injection molding processes, and may be made by other conventional manufacturing processes including thermoforming, machining and the like.

The ultrasonic horn used in the apparatus and process of the present invention is made from conventional materials including aluminum, stainless steel and the like.

Although this invention has been shown and described with respect to detailed embodiments thereof, it will be understood by those skilled in the art that various changes in form and detail thereof may be made without departing from the spirit and scope of the claimed invention.

We claim:

1. A method of riveting a suture tray package, comprising:

providing a top component having a top, a bottom, an outer periphery and a plurality of rivet members extending down from the bottom, the rivets members having free bottom ends;

providing a bottom component having a top, a substantially flat bottom, an outer periphery, a suture channel, and a plurality of rivet receiving holes extending through the bottom component for receiving the rivet members, and a counter bore extending into the bottom of the bottom component around each rivet receiving hole;

assembling the top component to the bottom component to form an assembly by substantially aligning the peripheries of the top and bottom components and aligning the rivets with corresponding rivet holes, and then moving the top and bottom components together such that the free ends of the rivets are substantially contained in the rivet receiving holes and counterbores surrounding the rivet holes;

providing an ultrasonic riveting apparatus comprising:

a frame;

a clamp member movably mounted to the frame, said clamp member having a cavity, a bottom surface, a top surface and openings in the top and bottom surfaces in communication with the cavity;

a base mounted to the frame for receiving the assembled bottom component and top component, the base having a top, a bottom, and a groove in the top for receiving the suture channel of the bottom component;

an ultrasonic horn member movingly mounted to the frame, said ultrasonic horn member having a substantially flat bottom surface, and said ultrasonic horn member moveable within the cavity of the clamp member; and, an ultrasonic generator connected to the horn member;

placing the assembly on the base member such that the bottom component is on top of the top component and the suture channel is substantially contained within the groove;

moving the clamp member to engage the bottom of the bottom member of the assembly;

moving the ultrasonic horn member through the cavity of the clamp member such that the bottom surface of the ultrasonic member engages the end of each rivet; and, energizing the horn with sufficient ultrasonic energy for a sufficient period of time to effectively heat and deform the ends of the rivets such that the ends of the rivets are contained within the counterbores surrounding the rivet holes, and the ends of the rivets are substantially flat and in alignment with the flat bottom surface of the bottom component.

2. The method of claim 1, wherein the top component additionally comprises a plurality of radially extending hinged doors to cover the suture channel.

3. The method of claim 1, wherein the top component additionally comprises at least one needle park member extending up from the top.

4. The method of claim 1 wherein the ultrasonic horn is moveable vertically.

5. The method of claim 1 wherein the clamping member is moveable vertically.

6. The method of claim 1 wherein the ultrasonic horn member exerts a force on the ends of the rivets.

7. The method of claim 1 wherein the clamping member exerts a downward force on at least part of the assembly.

* * * * *